(12) United States Patent
Kim et al.

(10) Patent No.: US 9,895,421 B2
(45) Date of Patent: Feb. 20, 2018

(54) PHARMACEUTICAL COMPOSITION HAVING PREVENTATIVE OR TREATMENT EFFECT ON INFLAMMATORY BOWEL DISEASES

(71) Applicant: University-Industry Cooperation Group of Kyung Hee University, Gyeonggi-do (KR)

(72) Inventors: Jin Ju Kim, Gyeonggi-do (KR); Eun Jung Ko, Seoul (KR); Eui Jeoung Lee, Seoul (KR)

(73) Assignee: University-Industry Cooperation Group of Kyung Hee University, Gyeonggi-Do (KR)

( * ) Notice: Subject to any disclaimer, the term of this patent is extended or adjusted under 35 U.S.C. 154(b) by 435 days.

(21) Appl. No.: 14/412,145

(22) PCT Filed: Jul. 3, 2013

(86) PCT No.: PCT/KR2013/005892
§ 371 (c)(1),
(2) Date: Dec. 30, 2014

(87) PCT Pub. No.: WO2014/007536
PCT Pub. Date: Jan. 9, 2014

(65) Prior Publication Data
US 2015/0164993 A1 Jun. 18, 2015

(30) Foreign Application Priority Data

Jul. 3, 2012 (KR) ........................ 10-2012-0072390

(51) Int. Cl.
| | |
|---|---|
| *A61K 36/53* | (2006.01) |
| *A61K 36/79* | (2006.01) |
| *A61K 36/64* | (2006.01) |
| *A61K 36/185* | (2006.01) |
| *A61K 38/20* | (2006.01) |
| *A61K 36/8965* | (2006.01) |
| *A61K 36/539* | (2006.01) |
| *A61K 36/804* | (2006.01) |
| *A61K 36/904* | (2006.01) |
| *A61K 36/65* | (2006.01) |
| *A61K 36/73* | (2006.01) |
| *A61K 35/618* | (2015.01) |
| *A61K 36/84* | (2006.01) |
| *A61K 36/738* | (2006.01) |
| *A61K 38/19* | (2006.01) |

(52) U.S. Cl.
CPC .......... *A61K 38/204* (2013.01); *A61K 35/618* (2013.01); *A61K 36/539* (2013.01); *A61K 36/65* (2013.01); *A61K 36/73* (2013.01); *A61K 36/738* (2013.01); *A61K 36/79* (2013.01); *A61K 36/804* (2013.01); *A61K 36/84* (2013.01); *A61K 36/8965* (2013.01); *A61K 36/904* (2013.01); *A61K 38/19* (2013.01); *A61K 38/191* (2013.01); *A61K 38/2006* (2013.01)

(58) Field of Classification Search
None
See application file for complete search history.

(56) References Cited

U.S. PATENT DOCUMENTS

| | | | | |
|---|---|---|---|---|
| 7,871,631 | B2 * | 1/2011 | Matsumoto | .......... A61K 31/047 424/278.1 |
| 2013/0296260 | A1 * | 11/2013 | Kitamura | ............... A61K 38/17 514/21.3 |
| 2013/0302844 | A1 * | 11/2013 | Ikegami | ............... A23C 9/1238 435/29 |

FOREIGN PATENT DOCUMENTS

| | | |
|---|---|---|
| KR | 100629311 B1 | 6/2006 |
| KR | 1020100103999 A | 9/2010 |
| KR | 1020110083917 A | 7/2011 |
| KR | 1020120008366 A | 1/2012 |
| KR | 1020120061725 A | 6/2012 |

* cited by examiner

Primary Examiner — Chris R Tate
Assistant Examiner — Randall Winston
(74) Attorney, Agent, or Firm — Cesari and McKenna, LLP

(57) ABSTRACT

The present invention relates to a pharmaceutical composition, which contains a mixture of extracts of Stemonae Radix, Asparagi Tuber, Scutellariae Radix, Schisandrae Fructus, Rehmanniae Radix Preparata, Armeniacae Semen, and Moutan Cortex Radicis, for suppressing the occurrence of inflammatory bowel diseases due to cigarette smoke, a method for preventing or treating inflammatory bowel diseases, a method for suppressing the expression of inflammatory cytokines by using the composition, and to a food composition, which contains a mixture of extracts of Stemonae Radix, Asparagi Tuber, Scutellariae Radix, Schisandrae Fructus, Rehmanniae Radix Preparata, Armeniacae Semen, and Moutan Cortex Radicis, for preventing or ameliorating inflammatory bowel diseases due to cigarette smoke. The pharmaceutical composition, according to the present invention, contains the mixture of extracts of Stemonae Radix, Asparagi Tuber, Scutellariae Radix, Schisandrae Fructus, Rehmanniae Radix Preparata, Armeniacae Semen, and Moutan Cortex Radicis, thereby reducing the level of MMP12 expression that is known to destroy IL-1β, TNF-α, IL-6 and MCP-1, which are inflammatory cytokines that accompany the inflammatory bowel diseases, elastin, and collagen, and thus can be widely used in developing a safe and effective inflammatory bowel disease treating agent.

4 Claims, 5 Drawing Sheets

[FIG. IA]
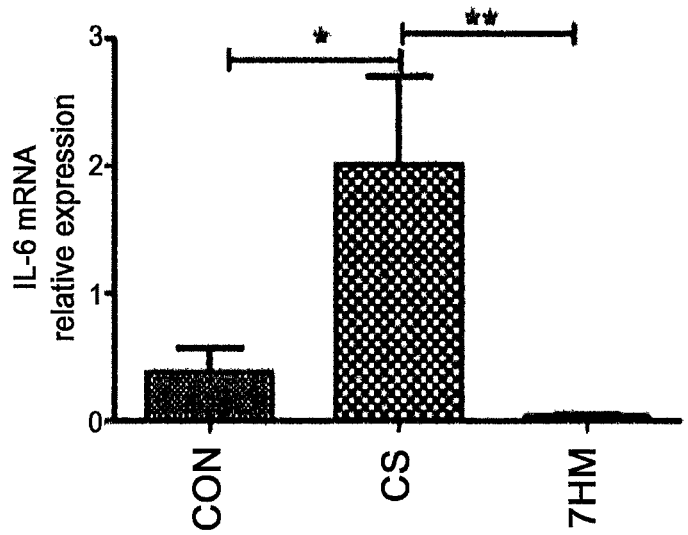
[FIG. IB]
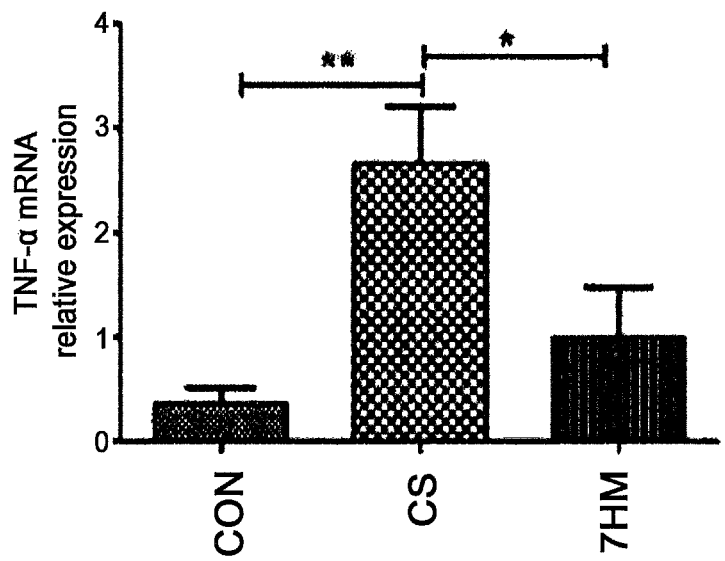

[FIG. IC]
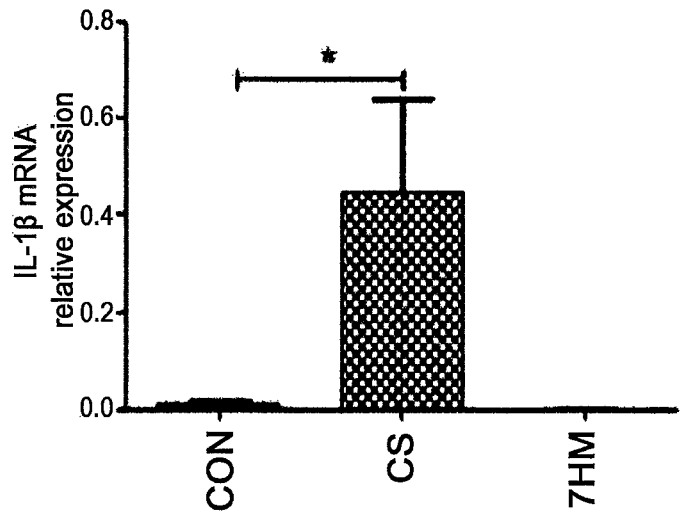
[FIG. ID]
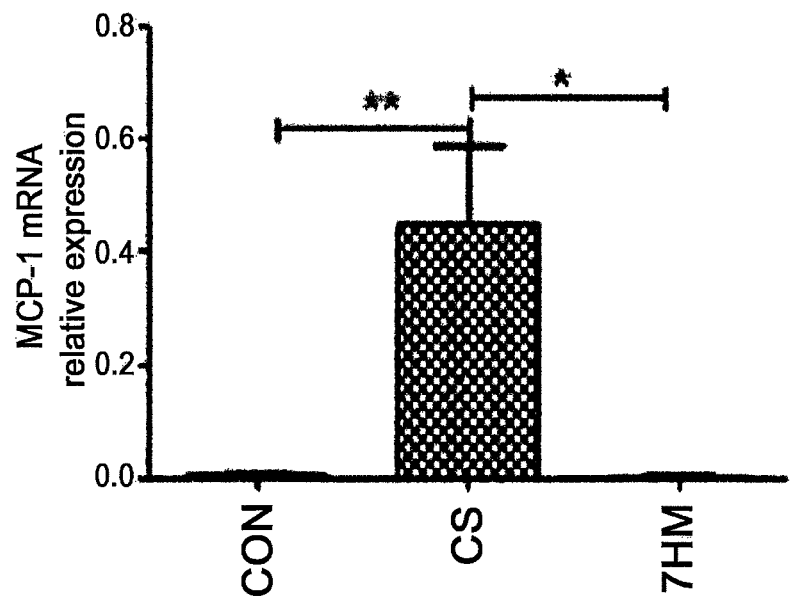

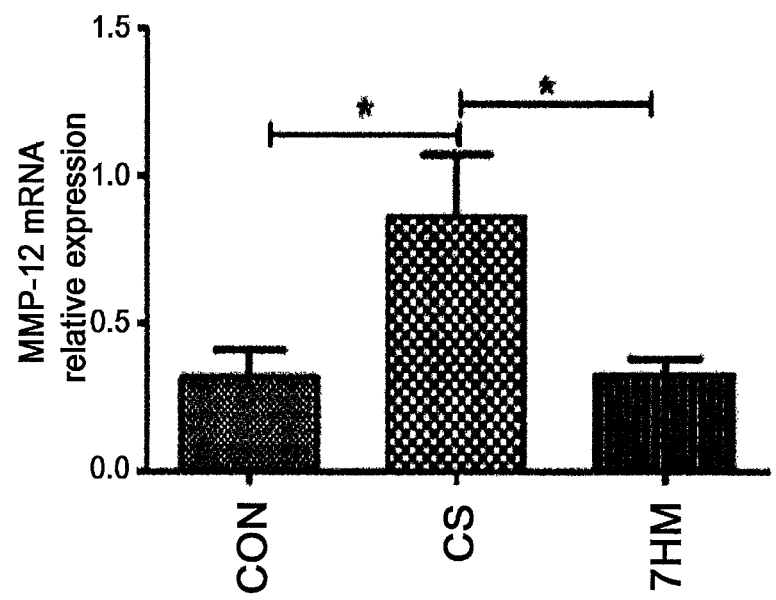
[FIG. IE]

[FIG. 2A]
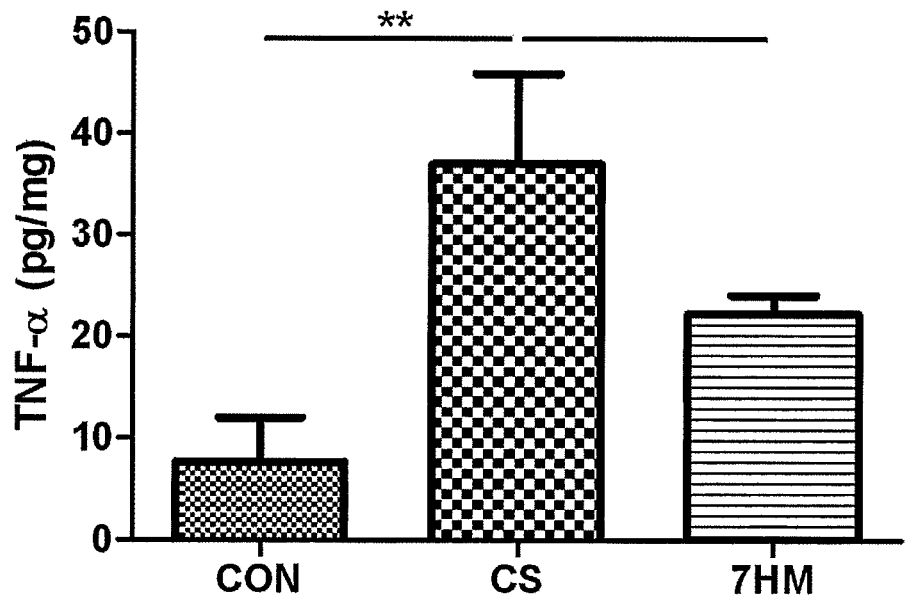
[FIG. 2B]
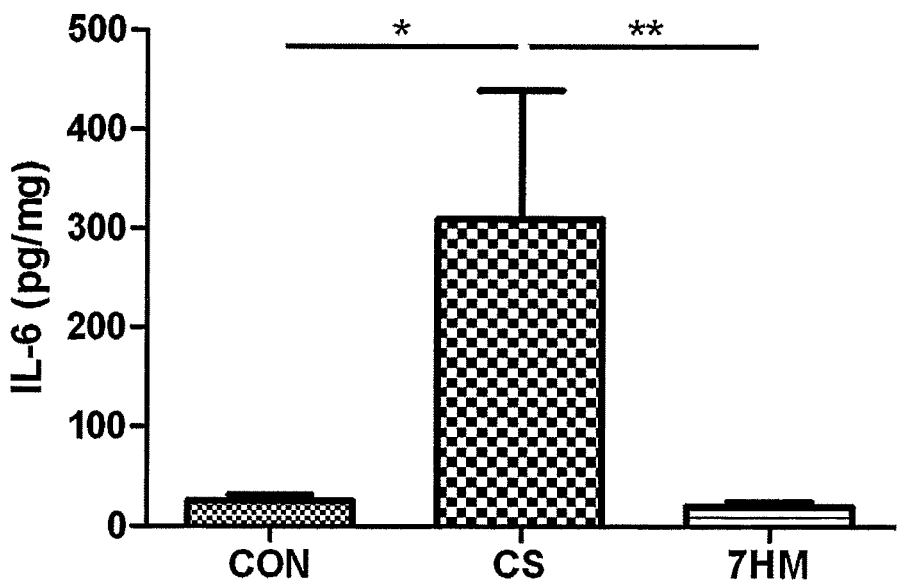

[FIG. 2C]
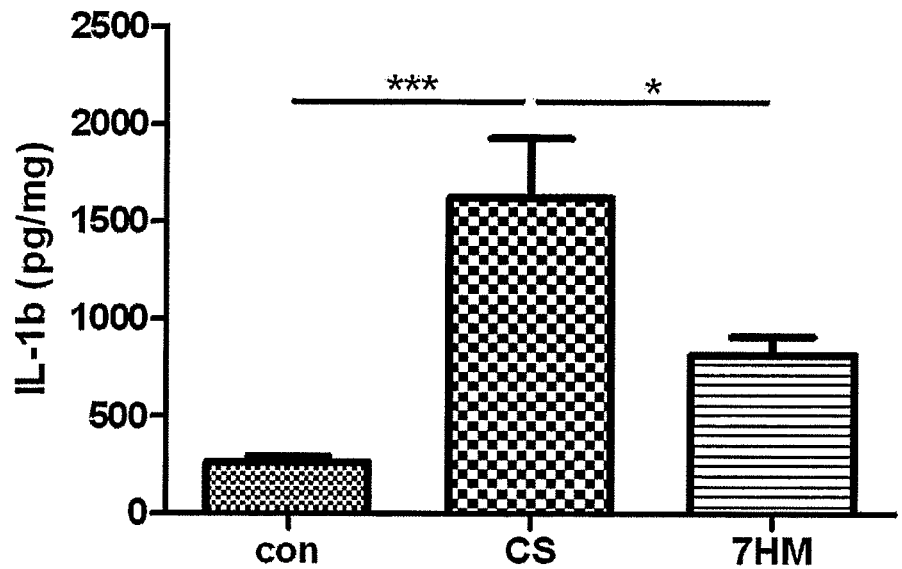
[FIG. 2D]
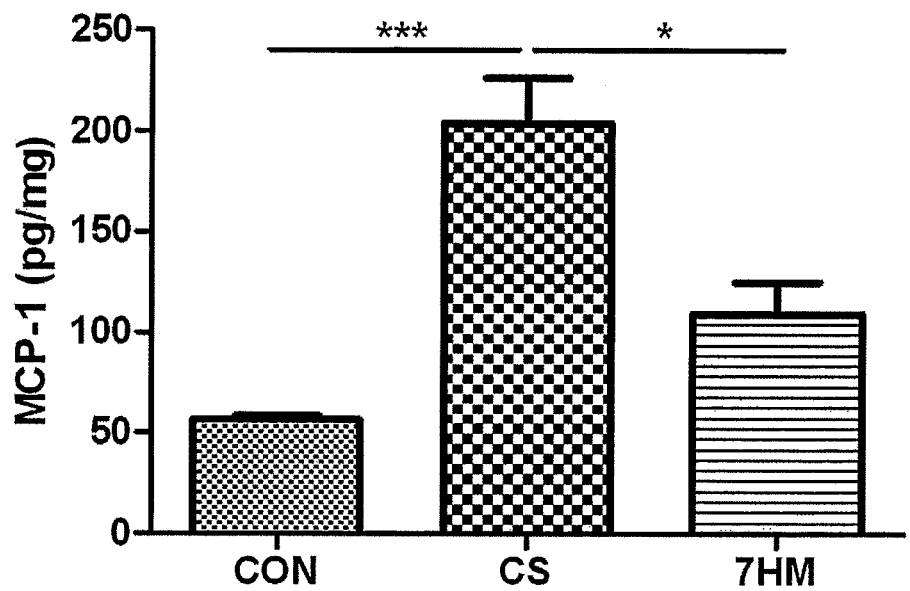

PHARMACEUTICAL COMPOSITION HAVING PREVENTATIVE OR TREATMENT EFFECT ON INFLAMMATORY BOWEL DISEASES

CROSS REFERENCE TO RELATED APPLICATIONS

This application is the National Stage of International Application No. PCT/KR2013/005892, filed on Jul. 3, 2013, which claims the benefit of Korean Application No. 10-2012-0072390, filed on Jul. 3, 2012. The contents of both applications are hereby incorporated by reference in their entirety.

BACKGROUND OF THE INVENTION

1. Field of the Invention

The present invention relates generally to a pharmaceutical composition for preventing or treating inflammatory bowel diseases, and more particularly, to a pharmaceutical composition comprising a mixture of extracts of Stemonae Radix, Asparagus Tuber, Scutellariae Radix, Schisandrae Fructus, Rehmanniae Radix Preparata, Armeniacae Semen, and Moutan Cortex Radicis, which can prevent the development of inflammatory bowel diseases due to cigarette smoke, a method for preventing or treating inflammatory bowel diseases using the composition, a method for inhibiting overexpression of inflammatory cytokines using the composition, and a food composition comprising a mixture of extracts of Stemonae Radix, Asparagus Tuber, Scutellariae Radix, Schisandrae Fructus, Rehmanniae Radix Preparata, Armeniacae Semen, and Moutan Cortex Radicis, which can prevent or ameliorate the development of inflammatory bowel diseases due to cigarette smoke.

2. Description of the Related Art

As is well known in the art, inflammatory bowel diseases (IBD), which generally begin to develop in adolescent years, cause chronic inflammation in the gastrointestinal tract and are accompanied by symptoms such as abdominal pain, fever, diarrhea, and melena. Inflammatory bowel diseases are generally divided into two types: ulcerative colitis (UC) and Crohn's disease (CD). Ulcerative colitis is a type of diffuse nonspecific inflammation of an unknown cause occurring in the colon, which mostly invades mucous membranes, frequently causes decay or ulcers and is accompanied by various systemic symptoms including bloody diarrhea, whereas Crohn's disease is a type of granulomatous inflammation of an unknown cause that develops ulcer, fibrosis, stenosis, and lesions in the entire digestive system from mouth to anus, and is accompanied by systemic symptoms such as abdominal pain, chronic diarrhea, fever, and malnutrition.

Although the exact cause of inflammatory bowel diseases has not been identified, allegedly they appear to occur due to a disorder in immune functions, in which factors such as innate immunity, production of cytokines, activation of CD4, etc., are known to be involved. In particular, cytokines are known to play an important role therein, and significantly increased levels of tumor necrosis cytokine (TNF-α), interleukin (IL)-1, IL-6, and IL-8 were observed in inflammatory lesions of patients with ulcerative colitis or Crohn's disease.

Examples of drugs used for treating inflammatory bowel diseases include steroid immunosuppressive agents, 5-aminosalicylic acid (5-ASA)-based drugs that block the production of prostaglandins (e.g., sulfasalazine), mesalazine, etc. However, they have little therapeutic effects and also cause serious side effects such as headaches, rashes, liver diseases, leucopenia, male infertility, etc., thus limiting the use of these drugs.

In this regard, the development of a therapeutic drug for treating the inflammatory bowel diseases without side effects will be very useful for safely and effectively treating patients with the diseases, but the development of the therapeutic drug has not yet been accomplished.

SUMMARY OF THE INVENTION

The inventors of the present invention, while endeavoring to develop a therapeutic agent without side effects derived from a natural substance, discovered that a composition comprising a mixture of extracts of Stemonae Radix, Asparagus Tuber, Scutellariae Radix, Schisandrae Fructus, Rehmanniae Radix Preparata, Armeniacae Semen, and Moutan Cortex Radicis can inhibit the expression of MMP12, which is known to destroy inflammatory cytokines, elastin, and collagen, and thus can be used for treating inflammatory bowel diseases, thereby completing the present invention.

Accordingly, the present invention has been made keeping in mind the above problems occurring in the prior art, and an objective of the present invention is to provide a pharmaceutical composition for preventing or treating inflammatory bowel diseases.

Another objective of the present invention is to provide a method for preventing or treating inflammatory bowel diseases using the pharmaceutical composition.

A further objective of the present invention is to provide a method for inhibiting the expression of inflammatory cytokines using the pharmaceutical composition.

A still further objective of the present invention is to provide a food composition for preventing or ameliorating inflammatory bowel diseases.

Advantageous Effects of the Invention

The pharmaceutical composition of the present invention comprises a mixture of extracts of Stemonae Radix, Asparagus Tuber, Scutellariae Radix, Schisandrae Fructus, Rehmanniae Radix Preparata, Armeniacae Semen, and Moutan Cortex Radicis and thus can reduce the expression level of MMP12, which is known to destroy inflammatory cytokines such as IL-1β, TNF-α, IL-6 and MCP-1, elastin, and collagen, accompanied with the inflammatory bowel diseases, thus being very useful in developing a safe and effective therapeutic agent for treating inflammatory bowel diseases.

BRIEF DESCRIPTION OF THE DRAWINGS

The above and other objectives, features and other advantages of the present invention will be more clearly understood from the following detailed description taken in conjunction with the accompanying drawings, in which:

FIG. 1A is a graph illustrating the change in the level of IL-6 mRNA by the treatment of the composition of the present invention;

FIG. 1B is a graph illustrating the change in the level of TNF-α mRNA by the treatment of the composition of the present invention;

FIG. 1C is a graph illustrating the change in the level of IL-1β mRNA by the treatment of the composition of the present invention;

FIG. 1D is a graph illustrating the change in the level of MCP-1 mRNA by the treatment of the composition of the present invention;

FIG. 1E is a graph illustrating the change in the level of MMP12 mRNA by the treatment of the composition of the present invention;

FIG. 2A is a graph illustrating the change in the level of TNF-α protein by the treatment of the composition of the present invention;

FIG. 2B is a graph illustrating the change in the level of IL-6 protein by the treatment of the composition of the present invention;

FIG. 2C is a graph illustrating the change in the level of IL-1β protein by the treatment of the composition of the present invention; and FIG. 2D is a graph illustrating the change in the level of MCP-1 protein by the treatment of the composition of the present invention.

DESCRIPTION OF THE PREFERRED EMBODIMENTS

In an aspect of the present invention to accomplish the above objectives, the present invention provides a pharmaceutical composition for preventing or treating inflammatory bowel diseases comprising a mixture of extracts of Stemonae Radix, Asparagus Tuber, Scutellariae Radix, Schisandrae Fructus, Rehmanniae Radix Preparata, Armeniacae Semen, and Moutan Cortex Radicis.

The present inventors, while performing studies to develop a therapeutic agent derived from a natural substance without side effects for treating inflammatory bowel diseases using various extracts of natural substances, had their attention drawn to the mixture of extracts of Stemonae Radix, Asparagus Tuber, Scutellariae Radix, Schisandrae Fructus, Rehmanniae Radix Preparata, Armeniacae Semen, and Moutan Cortex Radicis. As a result, they discovered that the mixture of extracts can reduce the amount of expression of MMP12, which is known to destroy inflammatory cytokines, elastin, and collagen, the levels of which are increased with the onset of inflammatory bowel diseases, which were induced in mice by their exposure to cigarette smoke. Accordingly, the mixture of extracts of the present invention can be used as an active ingredient of a pharmaceutical composition for preventing or treating inflammatory bowel diseases.

As used herein, the term "Stemonae Radix" refers to a tuberous root of *Stemona japonica* Miquel or of a plant of the same species, which, morphologically, is straight or a little bent as a waterproof-type, is thin at both ends, has a yellow-white wrinkled outer surface, and irregular vertical wrinkles. It is hard and easily broken, its broken surface is keratinous and white, and its skin is contracted to its center and yellow. Its pharmacological actions include an antitussive action, an expectorating action, an insecticidal action, an antibacterial action, etc. In the herbal medicine art, it has therapeutic effects on the treatment of severe coughs, colds, coughs, and pertussis resulting from tuberculosis, has a hemostatic action, an insecticidal action, and has been used for treating hives, dermatitis, scabies, etc.

As used herein, the term "Asparagus Tuber" refers to a perennial monocotyledon plant growing on the seashore and belonging to the family Veneridae of the order Veneroida, which, morphologically, has a short rhizome, numerous roots with sharp cylindrical ends extending out in all directions, a stem whose lower part has egg-shaped scaly pieces, a 1-2 m long green vine stem, and leaf-like branches being bundled into a set of 1-3 that are bent like a bow. Its pharmacological actions include an antitussive action, a diuretic action, a tonic action, etc.

As used herein, the term "Scutellariae Radix" refers to a perennial dinocotyledon plant growing in mountains and belonging to the family Lamiaceae of the order Tubiflorales, which morphologically has stems sprouted in clumps and has hairs and branches that are separated. The plant has opposing lanceolate leaves and has a blunt edge. In the art of herbal medicine, the root is used as an antipyretic agent, a diuretic agent, an antidiarrheal agent, a cholagogue agent, an anti-inflammatory agent, etc.

As used herein, the term "Schisandrae Fructus" refers to a fruit of a *Schisandra chinensis* Baillon plant, which, morphologically, has the shape of a thick red ball with a diameter of about 1 cm, wherein red juice and 1-2 reddish brown seeds are included therein and contains schizandrin, gomisin, citral, malic acid, etc. In the art of herbal medicine, the fruit is used as a tonic agent or a cardiac stimulant. Additionally, because it can strengthen pulmonary functions and has antitussive and expectorating actions, it thus can be used for treating coughs or thirst or the like.

As used herein, the term "Rehmanniae Radix Preparata" refers to a herbal raw material prepared by steaming followed by drying the *Rehmannia* root. In the art of herbal medicine, it is known to have a sweet taste with a feeling of bitterness and a warm property, and is thus used for treating cold waist and knees and pains thereon, menstrual disorder, dizziness, and darkening hairs.

As used herein, the term "Armeniacae Semen" refers to a seed of an apricot tree, which is relatively abundant in citric acid and malic acid, and also has high vitamin A content, and is thus known to mediate the metabolism. In the art of herbal medicine, its pharmacological actions include an antitussive action, a diuretic action, a diuretic action, a tonic action, constipation treatment, etc.

As used herein, the term "Moutan Cortex Radicis" refers to a herbal drug prepared using the root bark of *Paeonia suffruticosa* Andrews belonging to the family *Paeonia*, which, morphologically, are tubular bark pieces whose outer surface takes on a dark brown or brown color with a purple tint, and have lengthy vertical oval-shaped marks of lateral roots and horizontal wrinkles, wherein the inner surface is flat and takes on a light taupe or dark purple color, and its broken surface is rough, and white crystals are often attached to the inner surface and the broken surface. The pharmacological actions of the Moutan Cortex Radicis include an analgesic action, a sedative action, a fever-alleviating action, an anti-convulsion action, an anti-inflammation action, an anti-thrombotic action, an anti-allergic action, inhibition of gastric secretion, endometrial hyperemia, an antibacterial action, etc. In the art of herbal medicine, the Moutan Cortex Radicis is used for treating menstrual irregularity due to blood heatmenstrual pain, bruises, hematemesis, epistaxis, macules, bone aches due to consumptive fever, blood pressure increase, extravasated blood, contusion, furuncles, and early appendicitis, and used for anti-inflammatory analgesic treatment.

As used herein, the term "extract" may refer to a product obtained from Stemonae Radix, Asparagus Tuber, Scutellariae Radix, Schisandrae Fructus, Rehmanniae Radix Preparata, Armeniacae Semen, and Moutan Cortex Radicis used in the present invention by a conventional extraction method, or the product as such purchased commercially. Preferably, the extracts may be obtained using an extraction solvent such as water, a C1~C6 alcohol, hexane, chloroform, methyl acetate, butanol, etc., and more preferably, using an extraction solvent such as water, a C1~C6 alcohol, or a combination thereof, and most preferably, hot water or 70% ethanol.

As used herein, the term "a mixture of extracts" refers to a resultant product obtained by combining each of the individual extracts of Stemonae Radix, Asparagus Tuber, Scutellariae Radix, Schisandrae Fructus, Rehmanniae Radix Preparata, Armeniacae Semen, and Moutan Cortex Radicis, or a resultant product obtained by extraction of the mixture containing all of the above components.

In the present invention, the mixture of extracts may refer to a resultant product obtained by combining each of the individual extracts of Stemonae Radix, Asparagus Tuber, Scutellariae Radix, Schisandrae Fructus, Rehmanniae Radix Preparata, Armeniacae Semen, and Moutan Cortex Radicis, and the mixture of extracts may be used as an active ingredient of a composition for preventing, treating, or ameliorating inflammatory bowel diseases.

As used herein, the term "inflammatory bowel disease (IBD)" refers to a disease that induces an inflammation in the gastrointestinal tract with accompanying symptoms such as abdominal pain, fever, diarrhea, and melena. Inflammatory bowel diseases are generally divided into two types: ulcerative colitis (UC) and Crohn's disease (CD). Ulcerative colitis is a type of diffuse nonspecific inflammation of an unknown cause occurring in the colon, which mostly invades mucous membranes, frequently causes decay or ulcers and is accompanied by various systemic symptoms including bloody diarrhea, whereas Crohn's disease is a type of granulomatous inflammation of an unknown cause that develops ulcer, fibrosis, stenosis, and lesions in the entire digestive system from mouth to anus, and accompanies systemic symptoms such as abdominal pain, chronic diarrhea, fever, and malnutrition.

As used herein, the term "prevention" refers to all kinds of activities associated with the inhibition or delay of inflammatory bowel diseases by administering the pharmaceutical composition of the present invention.

As used herein, the term "treatment" refers to all kinds of activities associated with clinical intervention for the purpose of changing the natural process(es) of an individual or a cell to be treated, which may be performed while the clinical pathological state is still in progress or to prevent the occurrence of the same. Examples of the aimed purposes of the therapeutic effects may include preventing occurrence or recurrence of a given disease, alleviating the symptoms therefrom, reducing all the direct or indirect pathological results due to the disease, preventing metastasis, decreasing the progress of the disease, reducing or temporarily alleviating and ameliorating the disease, or improving prognosis of the disease.

In the present invention, preferably, the above treatment should be understood as treating inflammatory bowel diseases using the pharmaceutical composition comprising the mixture of extracts of the present invention.

The pharmaceutical composition of the present invention provided in the present invention may comprise a mixture of extracts containing each of the individual extracts of Stemonae Radix, Asparagus Tuber, Scutellariae Radix, Schisandrae Fructus, Rehmanniae Radix Preparata, Armeniacae Semen, and Moutan Cortex Radicis. Preferably, the amount of each extract to be comprised in the mixture of extracts may be, although not limited thereto, 2 to 6 parts by weight of the Stemonae Radix extract, 6 to 10 parts by weight of the Asparagus Tuber extract, 4 to 8 parts by weight of the Scutellariae Radix extract, 6 to 10 parts by weight of the Schisandrae Fructus extract, 14 to 18 parts by weight of the Rehmanniae Radix Preparata extract, 4 to 8 parts by weight of the Armeniacae Semen extract, and 6 to 10 parts by weight of the extract of Moutan Cortex Radicis, respectively; and more preferably, 4 parts by weight of the Stemonae Radix extract, 8 parts by weight of the Asparagus Tuber extract, 6 parts by weight of the Scutellariae Radix extract, 8 parts by weight of the Schisandrae Fructus extract, 16 parts by weight of the Rehmanniae Radix Preparata extract, 6 parts by weight of the Armeniacae Semen extract, and 8 parts by weight of the extract of Moutan Cortex Radicis. Additionally, the pharmaceutical composition of the present invention can reduce the amount of expression of MMP12, which is known to destroy inflammatory cytokines, elastin, and collagen, the levels of which are increased at the onset of the occurrence of inflammatory bowel diseases caused by cigarette smoke.

In an embodiment of the present invention, the mixture of Stemonae Radix, Asparagus Tuber, Scutellariae Radix, Schisandrae Fructus, Rehmanniae Radix Preparata, Armeniacae Semen, and Moutan Cortex Radicis was subjected to hot-water extraction to obtain a herbal drug composition (Example 1), and the mice administered with the herbal drug composition was exposed to cigarette smoke, and as a result, the mRNA levels of IL-6, TNF-$\alpha$, IL-1$\beta$ and MCP-1, which are inflammatory cytokines generated due to cigarette smoke, were reduced (FIGS. 1A through 1D), the mRNA level of MMP12, which is known to destroy elastin and collage, was reduced (FIG. 1E), and also the levels of each of the inflammatory cytokines proteins were reduced (FIGS. 2A through 2D).

Meanwhile, the pharmaceutical composition of the present invention may further comprise a suitable carrier, an excipient, or a diluent, conventionally used in the manufacture of a pharmaceutical composition. Specifically, the pharmaceutical composition may be prepared in the form of oral formulations such as powders, granules, tablets, capsules, suspensions, emulsions, syrups, and aerosols, external use formulations, suppositories, and sterile injection solutions, according to the conventional methods. In the present invention, examples of the carrier, the excipient, or the diluent to be comprised in the pharmaceutical composition are lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and base oil.

For formulations, a commonly used filler, extender, binder, humectant, disintegrant, surfactant, diluent, or excipient may be added. Examples of the solid formulations for oral administration are tablets, pills, powders, granules, capsules, etc., and the formulations are prepared by mixing at least one excipient, e.g., starch, calcium carbonate, sucrose or lactose, gelatin, etc., with the extract or fractions thereof. Additionally, lubricants such as magnesium stearate and talc may be used in addition to the simple excipients. Examples of liquid formulations for oral administration are suspensions, internal-use liquid medicines, emulsions, syrups, etc., and various excipients, e.g., humectants, sweeteners, fragrant, preservatives, etc., may be added in addition to the simple diluents such as water and liquid paraffin. Examples of formulations for parenteral administration are sterile aqueous solutions, non-aqueous solvents, suspensions, emulsions, lyophilized formulations, and suppositories. Examples of the non-aqueous solvents and suspensions may comprise propylene glycol, polyethylene glycol, a vegetable oil such as olive oil, injectable ester such as ethyl oleate, etc. Examples of the bases for the suppositories may comprise witepsol, macrogol, tween 61, cacao butter, laurinum, glycerogelatin, etc.

The amount of the mixture of extracts contained in the pharmaceutical composition according to an embodiment of the present invention may be ranging from 0.0001 wt % to 50 wt % relative to the total weight of the final composition, and more preferably, 0.01 wt % to 10 wt %, although not particularly limited thereto.

The pharmaceutical composition of the present invention may be administered in a pharmaceutically effective amount. As used herein, "a pharmaceutically effective amount" refers to an amount sufficient for the treatment of diseases at a reasonable benefit/risk ratio applicable to a medical treatment, and the level of the effective dose may be determined from factors including severity of illness, drug activity, age, body weight, health conditions, drug sensitivity of a subject, administration time, administration route and dissolution rate, length of treatment of the pharmaceutical composition of the present invention, drug(s) used in combination with or simultaneously with the pharmaceutical composition of the present invention, and other factors well known in the medical field. The pharmaceutical composition of the present invention may be administered as an individual therapeutic agent or in combination with other therapeutic agent(s), and also sequentially or simultaneously with the conventional therapeutic agent(s). Additionally, the pharmaceutical composition of the present invention may be administered as a single dose or in multiple divided doses. Additionally, it is important that the least amount which can achieve the maximum effect without any side effects be administered in consideration of all the factors described above.

The dose of the pharmaceutical composition of the present invention may be determined by a skilled person in the art considering the intended use(s), severity of disease(s), age, body weight, sex and anamnesis of a subject, or the kinds of ingredients used as active ingredient(s), etc. For example, the pharmaceutical composition of the present invention may be administered in the range of from about 1 mg/kg/day to about 20 mg/kg/day for mammals including humans, and preferably from 1 mg/kg/day to 10 mg/kg/day. The pharmaceutical composition of the present invention may be administered once daily or in a few divided doses, although administration is not particularly limited thereto.

In another aspect of the present invention to achieve the objectives, there is provided a method for preventing or treating inflammatory bowel diseases comprising administering a pharmaceutically effective amount of the pharmaceutical composition containing the mixture of extracts of the present invention as an active ingredient to a subject having a risk of developing an inflammatory bowel disease or having the inflammatory bowel disease.

As described above, the mixture of extracts of the present invention can be used as an active ingredient of the pharmaceutical composition for preventing or treating inflammatory bowel diseases, and it thus can be used for preventing or treating inflammatory bowel diseases.

As used herein, the term "subject" refers to all kinds of animals including humans having a risk of inflammatory bowel disease(s) or having inflammatory bowel disease(s). The administration of the pharmaceutical composition of the present invention can alleviate or treat the inflammatory bowel disease(s) of the subject.

As used herein, the term "alleviation" refers to all kinds of activities associated with ameliorating or advantageously changing the status of inflammatory bowel disease(s) by the administration of the pharmaceutical composition of the present invention.

As used herein, the term "administration" refers to an activity of introducing the pharmaceutical composition of the present invention to a subject by an appropriate method, and the pharmaceutical composition may be administered via various routes of oral or parenteral routes as long as they can deliver the same to the target tissues.

Regarding the method for treating inflammatory bowel diseases, the pharmaceutical composition may be administered via any general routes as long as they can deliver the same to the target tissues. According to the intended purposes, the pharmaceutical composition of the present invention may be administered via intraperitoneal administration, intravenous administration, intramuscular administration, subcutaneous administration, intracutaneous administration, oral administration, intranasal administration, intrapulmonary administration, and intrarectal administration, although not particularly limited thereto. Additionally, the pharmaceutical composition may be administered via any apparatus that enables to transport the active ingredient to a target cell.

In a further aspect of the present invention to achieve the objectives, there is provided a method for inhibiting the expression of inflammatory cytokines including treating the tissues or cells having overexpression of inflammatory cytokines with the pharmaceutical composition of the present invention.

As used herein, the term "inflammatory cytokines" refers to cytokines which induce inflammatory reactions in the body, and the inflammatory cytokines may include IL-1β, TNF-α, IL-6, MCP-1, etc., although are not limited thereto.

In a further aspect of the present invention to achieve the objectives, there is provided a food composition for preventing or ameliorating inflammatory bowel diseases comprising a mixture of extracts of Stemonae Radix, Asparagus Tuber, Scutellariae Radix, Schisandrae Fructus, Rehmanniae Radix Preparata, Armeniacae Semen, and Moutan Cortex Radicis.

The Stemonae Radix, Asparagus Tuber, Scutellariae Radix, Schisandrae Fructus, Rehmanniae Radix Preparata, Armeniacae Semen, and Moutan Cortex Radicis comprised in the mixture of extracts have long been used as herbal raw materials and their safety has been approved accordingly. Therefore, they can be used as a food composition.

The mixture of extracts of Stemonae Radix, Asparagus Tuber, Scutellariae Radix, Schisandrae Fructus, Rehmanniae Radix Preparata, Armeniacae Semen, and Moutan Cortex Radicis may be comprised in the range from 0.01 wt % to 100 wt % relative to the total weight of the food composition, preferably from 1 wt % to 80 wt %. When the food is beverage it may be comprised in the range from 1 g to 30 g per 100 mL of the food composition, preferably from 3 g to 20 g. Additionally, the composition may further comprise additional ingredients which may be conventionally used in food compositions to improve smell, taste, sight, etc., e.g., vitamins A, C, D, E, B1, B2, B6, B12, niacin, biotin, folate, panthotenic acid, etc. Additionally, the composition may further comprise minerals such as Zn, Fe, Ca, Cr, Mg, Mn, Cu, etc. Additionally, the composition may further comprise amino acids such as lysine, tryptophan, cysteine, valine, etc. Additionally, the composition may further comprise food additives such as preservatives (potassium sorbate, sodium benzoate, salicylic acid, dehydro sodium acetate, etc.), disinfectants (bleaching powder, higher bleaching powder, sodium hypochlorite, etc.), antioxidants (butylhydroxyanisole (BHA), butylhydroxytoluene (BHT), etc.), coloring agents (tar color, etc.), color-developing agents (sodium nitrite, etc.), bleaching agents (sodium sulfite), seasonings (monosodium glutamate (MSG), etc.), sweeteners (dulcin, cyclemate, saccharin, sodium, etc.), flavors (vaniline, lactones, etc.), swelling agents (alum, potassium D-hydrogn tartate, etc.), fortifiers, emulsifiers, thickners (adhesive pastes), film-forming agents, gum base agents, antifoaming agents, solvents, improvers, etc. The food additives may be selected according to the food kinds and used in an appropriate amount.

Additionally, functional foods for preventing or ameliorating inflammatory bowel diseases may be manufactured using the food composition containing the mixture of extracts of Stemonae Radix, Asparagus Tuber, Scutellariae Radix, Schisandrae Fructus, Rehmanniae Radix Preparata, Armeniacae Semen, and Moutan Cortex Radicis.

Specifically, processed foods having a good shelf-life with a modified property of agricultural products, livestock products, or marine products applied thereto, may be manufactured using the food composition. Examples of the processed foods may comprise cookies, beverages, alcoholic beverages, fermented foods, canned foods, milk-processed foods, meat-processed foods, noodles, etc. Examples of the cookies comprise biscuits, pies, cakes, breads, candies, jellies, gums, cereals (meal substitutes such as grain flakes). Examples of the beverages comprise carbonated soft drinks, functional isotonic drinks, juices (e.g., apple-, pear-, grape-, aloe-, tangerine-, peach-, carrot-, tomato juices, etc.), sweet rice drinks, etc. Examples of the alcoholic beverages comprise refined rice wine, whisky, soju (Korean distilled spirits), beer, liquors, fruits wine, etc. Examples of the fermented foods comprise soy sauce, bean paste, red pepper paste, etc. Examples of the canned foods comprise seafood canned foods (e.g., canned tuna, mackerel, mackerel pike, conch, etc.), livestock canned foods (canned beet pork, chicken, turkey, etc.), agricultural canned foods (canned corn, peach, pineapple, etc.). Examples of milk-processed foods comprise cheese, butter, yogurt, etc. Examples of meat-processed foods comprise pork cutlets, beef cutlets, chicken cutlets, sausages, sweet and sour porks, nuggets, neobiani, etc. Examples of noodles comprise sealed and packed fresh noodles. Additionally, the composition may be used for manufacturing retort foods, soups, etc.

As used herein, the term "functional food", which has the same meaning as the term "for special health use (FoSHU)", refers to a food with high effects in medicinal and medical treatment, modulating so as to efficiently exhibit a body modulating function as well as provide nutrients. The functional food may be manufactured in various forms including tablets, capsules, powders, granules, liquids, pills, etc., in order to obtain useful effects for the prevention or amelioratement of inflammatory bowel diseases.

Hereinafter, the present invention will be explained in greater detail through the following examples as set forth herein below, but they are disclosed for illustrative purposes only and are not to be construed as limiting the scope of the present invention.

EXAMPLE 1

Preparation of Samples

A mixture of 4 g of dried powder of Stemonae Radix hot-water extract, 8 g of dried powder of Asparagus Tuber, 6 g of dried powder of Scutellariae Radix hot-water extract, 8 g of dried powder of Schisandrae Fructus hot-water extract, 16 g of dried powder of Rehmanniae Radix Preparata, Armeniacae Semen hot-water extract, and 6 g of dried powder of bark of Paeonia suffruticosa Andrews hot-water extract, which were purchased from SUN TEN (Taipei, Taiwan), was dissolved in water, and filtered to obtain the resulting liquid composition to be used as a sample for oral administration for mice.

EXAMPLE 2

Induction of Inflammation Bowel Diseases (IBD) by Treatment with Cigarette Smoke Cigarettes are known to induce inflammatory bowel diseases (IBD) (Gareth A O Thomas, et al., Postgrad. Med. J., 76(895):273-279, 2000 May) and thus mice were exposed to cigarette smoke to induce inflammatory bowel diseases in the mice.

First, six-week old female C57BL/6 mice with body weights ranging from 20 g to 25 g were given ad libitum access to food and water, the breeding room was set to a temperature from 21° C. to 24° C. with a humidity of 40% to 60%, and the light-dark cycle was controlled at 12 hour intervals.

The thus-bred mice were orally administered with the liquid composition obtained in Example 1 at a dose of 100 mg/kg, placed into a smoking chamber, exposed to cigarette smoke by the smoking of 3 reference cigarettes 3R4F (University of Kentucky, Lexington, Ky.) for 30 minutes, kept therein for 30 minutes after removing the cigarette smoke therefrom, the cigarette smoke treatment process was repeated 4 times, and the entire cigarette smoke treatment process was performed once daily five times per week for a period of three weeks, thereby inducing inflammatory bowel diseases (IBD) in the mice and using them as the experimental group. In particular, the mice not treated with cigarette smoke were used as a control group (CON), the mice exposed to cigarette smoke but not treated with the liquid composition prepared in Example 1 were used as a comparative group (CS), and the number of mice assigned to each group was three for the control and the comparative groups, and two for the experimental group (7HM).

EXAMPLE 3

Effect of a Pharmaceutical Composition on Inflammatory Bowel Diseases

Example 3-1

Evaluation of the Effect of a Pharmaceutical Composition at mRNA Level

First, the mice in the control group, the comparative group, and the experimental group obtained in Example 2 were sacrificed and colorectal tissues were collected from the mice of each groups. Total RNA was obtained from the thus-collected colorectal tissues using the RNeasy Mini kit (QIAGEN, USA). Specifically, to each of the colorectal tissues was added 600 µL of RLT buffer solution to destroy cells, 600 µL of 70% ethanol as then further added, and the resulting solution was mixed. After adding 700 µL of the mixture into an RNeasy mini column of the RNeasy Mini kit and centrifuging it at 8,000×g for 15 seconds, the residual solution was added with 700 µL of RW1 buffer included in the above kit, centrifuged at 8,000×g for 15 seconds, and the residual solution was collected. Then, to the residual solution was added 500 µL of RPE buffer solution included in the above kit, centrifuged at 8,000×g for 15 seconds, and the residual solution was collected. The resulting residual solution was added with 50 μL of RNase free water, centrifuged at 8,000×g for 1 minute to finally obtain the total RNA. The thus-obtained total RNA was quantitated via spectrophotometer (ND-1000, NanoDrop Technologies Inc. USA), electrophoresed on a 1% agarose gel, and stained with ethidium-bromide (Et-Br, Sigma-Aldrich, USA) for evaluating its state.

Meanwhile, the thus-obtained total RNA was analyzed via real-time RT-PCR. For the above analysis, cDNA was obtained via RT-PCR (95° C.: 15 sec and 60° C.: 1 min, 40 cycles) using 2 μg of the thus-obtained total RNA, SYBR Green I Master Mix (Applied Biosystems, Foster City, Calif., USA) and primers (Genotech Inc., Korea). A real-time PCR was performed by applying the thus-obtained cDNA to the Applied Biosystems 7300 Real time PCR System, and the mRNA levels of MMP12, which is known to destroy inflammatory cytokines such as IL-6, TNF-α, IL-1β and MCP-1, and elastin and collagen, of the mice in the control group, the comparative group, and the experimental group were compared (FIGS. 1A through 1E).

FIG. 1A is a graph illustrating the change in the level of IL-6 mRNA by the treatment of the composition of the present invention; FIG. 1B is a graph illustrating the change in the level of TNF-α mRNA by the treatment of the composition of the present invention; FIG. 1C is a graph illustrating the change in the level of IL-1β mRNA by the treatment of the composition of the present invention; FIG. 1D is a graph illustrating the change in the level of MCP-1 mRNA by the treatment of the composition of the present invention; FIG. 1E is a graph illustrating the change in the level of MMP12 mRNA by the treatment of the composition of the present invention; FIG. 2A is a graph illustrating the change in the level of TNF-α protein by the treatment of the composition of the present invention; FIG. 2B is a graph illustrating the change in the level of IL-6 protein by the treatment of the composition of the present invention; FIG. 2C is a graph illustrating the change in the level of IL-1β protein by the treatment of the composition of the present invention; and FIG. 2D is a graph illustrating the change in the level of MCP-1 protein by the treatment of the composition of the present invention.

As illustrated in FIGS. 1A through 1E, the control group (CON) not treated with cigarette smoke showed low mRNA levels of IL-6, TNF-α, MCP-1 and MMP12, whereas the comparative group (CS) treated with only cigarette smoke showed a drastic increase in the mRNA levels of IL-6, TNF-α, IL-1β, MCP-1 and MMP12, and the experimental group (7HM), administered with the pharmaceutical composition of the present invention prior to their exposure to cigarette smoke, showed inhibitions of the increase in mRNA levels of IL-6, TNF-α, IL-1β, MCP-1 and MMP12 induced by cigarette smoke.

EXAMPLE 3-2

Evaluation of the Effect of a Pharmaceutical Composition at Protein Level

First, the mice in the control group, the comparative group, and the experimental group obtained in Example 2 were sacrificed and colorectal tissues were collected from the mice of each group. Then, the colorectal tissues had 500 μL of T-per solution added and the cells were destroyed by a homogenizer. The homogenized cells were placed on ice for 15 minutes and then vortexed for 15 seconds, the entire process of which was repeated 4 times, and the resultant was centrifuged at 14,000×g at 4° C. for 20 minutes to thereby obtain supernatants for each group.

Meanwhile, the respective antibodies corresponding to each of the inflammatory cytokines (TNF-α, IL-6, IL-1β or MCP-1) were coated on the substrates of an ELISA kit and placed them at 4° C. overnight. Then, each of the substrates was blocked by adding an assay diluent thereonto, and treated with the supernatants for each group, added with detection antibodies of the ELISA kit, added with the TMB solution of the ELISA kit to induce a color reaction. Then, the absorbance of the resulting substrates was measured by applying it to an ELISA reader and compared with each other (FIGS. 2A through 2D).

FIG. 2A is a graph illustrating the change in the level of TNF-α protein by the treatment of the composition of the present invention; FIG. 2B is a graph illustrating the change in the level of IL-6 protein by the treatment of the composition of the present invention; FIG. 2C is a graph illustrating the change in the level of IL-1β protein by the treatment of the composition of the present invention; and FIG. 2D is a graph illustrating the change in the level of MCP-1 protein by the treatment of the composition of the present invention.

As illustrated in FIGS. 2A through 2D, the comparative group (CS) treated with only cigarette smoke using 3R4F cigarettes showed a rapid increase in the levels of all the inflammatory cytokines, compared to that of the control group (CON), whereas, when treated with a mixture of extracts (7HM), the levels of all the inflammatory cytokines decreased.

Consequently, based on the results of Examples 3-1 and 3-2, it was confirmed that the mixture of extracts provided in the present invention has an inhibitory effect against the generation of inflammatory cytokines induced by cigarette smoke, and thus it has a therapeutic effect for preventing or treating inflammatory bowel diseases.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for treating ulcerative colitis or Crohn's disease in a subject in need thereof comprising administering to said subject a pharmaceutically effective amount of a pharmaceutical composition comprising a mixture of extracts of Stemonae Radix, Asparagus Tuber, Scutellariae Radix, Schisandrae Fructus, Rehmanniae Radix Preparata, Armeniacae Semen, and Moutan Cortex Radicis.

2. The method of claim 1, wherein the mixture of extracts comprises 2 to 6 parts by weight of the Stemonae Radix-extract, 6 to 10 parts by weight of the Asparagus Tuber extract, 4 to 8 parts by weight of the Scutellariae Radix extract, 6 to 10 parts by weight of the Schisandrae Fructus extract, 14 to 18 parts by weight of the Rehmanniae Radix Preparata extract, 4 to 8 parts by weight of the Armeniacae Semen extract, and 6 to 10 parts by weight of the extract of Moutan Cortex Radicis.

3. The method of claim 1, wherein the extracts are water extracts of Stemonae Radix, Asparagus Tuber, Scutellariae Radix, Schisandrae Fructus, Rehmanniae Radix Preparata, Armeniacae Semen, and Moutan Cortex Radicis.

4. The method of claim 1, wherein the pharmaceutical composition further comprises a pharmaceutically acceptable carrier, excipient, or diluents.

\* \* \* \* \*